United States Patent [19]

Miller

[11] Patent Number: 4,513,248
[45] Date of Patent: Apr. 23, 1985

[54] FLUID CONDUCTIVITY SENSOR

[75] Inventor: Francis M. Miller, Snyder, N.Y.

[73] Assignee: Conax Corporation, Buffalo, N.Y.

[21] Appl. No.: 462,913

[22] Filed: Feb. 1, 1983

Related U.S. Application Data

[63] Continuation-in-part of Ser. No. 207,340, Nov. 17, 1980, Pat. No. 4,382,231.

[51] Int. Cl.³ .............................................. G01N 27/02
[52] U.S. Cl. .............................. 324/439; 244/151 B; 340/620; 361/251
[58] Field of Search ................... 244/151 B; 340/620; 361/251; 73/304 R; 324/439, 446, 449, 450

[56] References Cited

U.S. PATENT DOCUMENTS

| | | | |
|---|---|---|---|
| 3,498,131 | 3/1970 | Rickey | 340/620 |
| 3,910,457 | 10/1975 | Sutliff et al. | 222/5 |
| 4,024,440 | 5/1977 | Miller | 361/251 |
| 4,137,527 | 1/1979 | Tennenhouse et al. | 240/620 |
| 4,227,190 | 10/1980 | Kelley et al. | 340/604 |
| 4,253,628 | 3/1981 | Marek | 244/151 A |
| 4,382,231 | 5/1983 | Miller | 324/439 |

Primary Examiner—Michael J. Tokar
Attorney, Agent, or Firm—Christel, Bean & Linihan

[57] ABSTRACT

Apparatus for sensing the electrical conductivity of fluid which can be used to detonate an electro explosive device for operating a release mechanism for uncoupling a parachute canopy from its load upon landing in water. An operating network connected to an ignition capacitor and to a conductivity sensing circuit and connected in controlling relation to a semiconductor switch has a voltage independent portion which controls the time at which the semiconductor switch is closed to define a discharge path to detonate the electro explosive device independent of the rate of voltage rise on the ignition capacitor. The operating network also has a voltage dependent portion which when a voltage of predetermined magnitude is developed on the conductivity sensing circuit in response to fluid not having the predetermined condition of conductivity, the voltage dependent portion closes the semiconductor switch to define the discharge path when the energy level is insufficient to detonate the electro explosive device. A regulated current source is connected in relation to the conductivity sensing circuit and to the electrodes thereof in a manner placing the circuit voltage across the electrodes when the conductivity of the fluid is below a predetermined magnitude so that the sensing circuit does not respond thereto and placing the circuit voltage across the sensing circuit when the conductivity of the fluid is greater than a predetermined magnitude. The apparatus is operated from a battery, and the electrodes are of dissimilar metals so selected and connected relative to the polarity portions of the circuit to maximize utilization of the battery output voltage.

24 Claims, 6 Drawing Figures

FLUID CONDUCTIVITY SENSOR

CROSS REFERENCE TO A RELATED APPLICATION

This application is a continuation-in-part of my pending application Ser. No. 207,340 filed Nov. 17, 1980, now U.S. Pat. No. 4,382,231, and entitled "Fluid Conductivity Sensor".

BACKGROUND OF THE INVENTION

This invention relates to the art of sensing the electrical conductivity of fluid, and more particularly to a new and improved apparatus for sensing and signalling the presence of liquid having a predetermined electrical conductivity.

One area of use of the present invention is detonating an electro explosive device of a release mechanism for uncoupling a parachute canopy upon landing in water, although the principles of the present invention can be variously applied. An important consideration in the design of such release mechanisms is preventing accidential detonation arising, for example, from exposure of the sensor to rain, salt water spray and fog along with component failure. However, whatever measures are provided to prevent accidental detonation should not interfere with normal operation of the sensor. In addition, conductivity sensing apparatus used with such release mechanisms is battery operated, and it would be highly desirable to provide such apparatus which maximizes the use of available battery voltage.

SUMMARY OF THE INVENTION

It is, therefore, a primary object of this invention to provide a new and improved apparatus for sensing the electrical conductivity of fluid.

It is a more particular object of this invention to provide such apparatus which is operative in response to fluid having a predetermined condition of conductivity and which is not susceptible to inadvertent or accidental operation in response to fluid not having such predetermined condition of conductivity.

It is a further object of this invention to provide such apparatus in which accidental or inadvertent operation is prevented in a manner not interfering with normal operation of the apparatus.

It is a further object of this invention to provide such apparatus which is battery operated and which maximizes use of the available voltage from the battery.

It is a further object of this invention to provide such apparatus for use with an electro explosive device of a release mechanism for uncoupling a parachute canopy from its load upon landing in water.

The present invention provides apparatus for sensing the electrical conductivity of fluid wherein a conductivity sensing circuit in response to a pair of electrodes being exposed to fluid having a predetermined condition of conductivity, for example predetermined minimum conductivity under conditions of exposure involving a predetermined minimum time rate of change of conductivity between the electrodes, applies a voltage to the control terminal of a semiconductor device switching the device into a conducting state to define a current flow path through a load connected to the device. The circuit can be used to detonate an electro explosive device in which case the load includes an ignition capacitor. A semiconductor switch defines a discharge path for the ignition capacitor through the electro explosive device. An operating network connected to the ignition capacitor and to the conductivity sensing circuit and connected in controlling relation to the semiconductor switch has a voltage independent portion which controls the time at which the semiconductor switch is closed to define the discharge path to detonate the electro explosive device independent of the rate of voltage rise on the ignition capacitor. The operating network also has a voltage dependent portion which is connected to the conductivity sensing network in a manner bypassing the semiconductor device and connected to the semiconductor switch. When a voltage of predetermined magnitude is developed on the conductivity sensing circuit in response to fluid not having the predetermined condition of conductivity, the voltage dependent portion closes the semiconductor switch to define the discharge path when the energy level is insufficient to detonate the electro explosive device. A latching or holding portion can be provided in the operating network to maintain the semiconductor switch closed in response to operation of the voltage dependent portion of the network. In order to prevent operation of the voltage dependent portion and latching portions of the network under certain conditions of fluid conductivity, a regulated current source is connected in relation to the sensing circuit and to the electrodes in a manner placing the circuit voltage across the electrodes when the conductivity of the fluid is below a predetermined magnitude and placing the major portion of the voltage across the sensing circuit when the conductivity of the fluid is greater than a predetermined magnitude. The apparatus is operated from a battery, and the electrodes are of dissimilar metals so selected and connected relative to the polarity portions of the circuit to maximize utilization of the battery output voltage. The electrodes are shaped to maximize the surface area exposed to the fluid without imparting operation thereof.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENT

Figure 1:
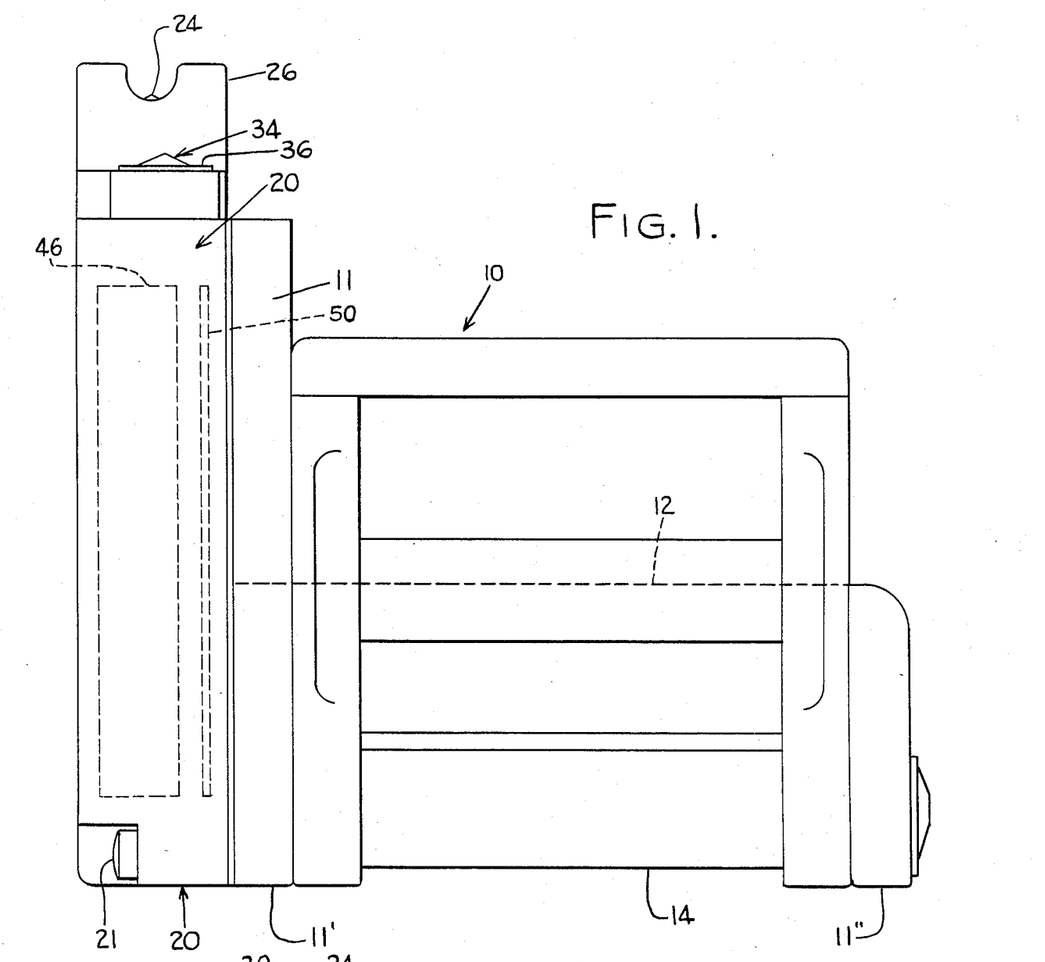
FIG. 1 is an elevational view showing an illustrative canopy release mechanism with which the present invention can be utilized.
Figure 2:
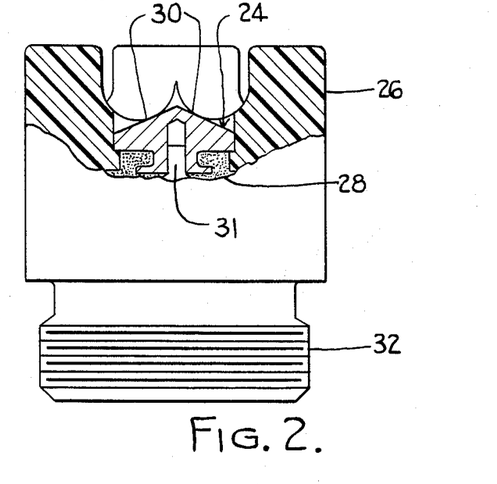
FIG. 2 is an enlarged fragmentary elevational view, partly in section, of one of the sensing electrodes in the apparatus of FIG. 1.
Figure 3:
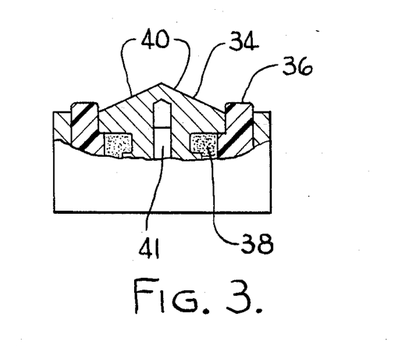
FIG. 3 is an enlarged elevational view, partly in section, of the other sensing electrode in the apparatus of FIG. 1.

Referring now to FIGS. 1 and 2, the apparatus of the present invention, generally speaking, is for sensing the electrical conductivity of a fluid, and one particular use illustrated herein is with a release mechanism for uncoupling a parachute canopy from its load upon landing in water. FIG. 1 illustrates a portion of a form of canopy release mechanism wherein the locking bar buckle half or body 10 of an illustrative canopy release assembly is shown. A canopy adjuster (not shown) is coupled to the buckle half or canopy release body 10 under control of a conventional double acting manually operable latch mechanism (not shown) in a known manner. An adapter plate 11 has arms 11', 11'' which are joined by a web 12 spanning the canopy release body 10. In the release mechanism shown, a detachable sleeve 14 replaces the existing pin, sleeve and retaining screw (not shown) of the usual canopy assembly. The releasing sleeve 14 has a longitudinal bore in which a release piston (not shown) is positioned. The left hand end of the piston as viewed in FIG. 1 extends beyond sleeve 14 into one end of a plug (not shown) which is fitted into the adapter plate arm 11' and extends into an opening in one arm of the buckle yoke to receive the end of the piston. The opposite end of sleeve 14, i.e. the right hand end as viewed in FIG. 1, is held in place by a bushing (not shown) which is seated in the open end of the sleeve and extends into an opening in the other arm of the buckle yoke. The piston and bushing can be held in position by shear pins to maintain the mechanism in an engaged position.

The plug associated with the left hand end of the piston as viewed in FIG. 1 contains an electro explosive device (not shown in FIG. 1) and which is adapted to be fired by operation of the fluid conductivity sensor of the present invention. Typically, the device includes a cartridge at the end adjacent the piston and a pair of electrical leads extending from the opposite end of the electro explosive device for supplying electrical current thereto. By way of example, an electro explosive device which will operate satisfactorily in this apparatus is available commercially from Conax Corporation Buffalo, N.Y. under the designation Part CC-131.

A housing generally designated 20 is attached to adapter plate 11 by suitable means, for example mounting screws one of which is designated 21. One end of housing 20 is provided with sensing electrode means. In particular, a first electrode 24 is located within an open ended cup shaped formation 26 of insulative material, for example Teflon, for electrically insulating electrode 24 from the remainder of the housing as shown in FIG. 2. An insulating epoxy 28 is provided for positioning and holding electrode 24 in place. The electrode 24 is provided with a conical outer surface 30 for a purpose to be described. A pin 31 fitted in the body of electrode 24 faciliates making electrical connection to a circuit in the apparatus. The entire electrode structure can be removably connected in housing 20 by means of a threaded end formation 32. There is provided a second electrode 34 at the same end of the housing in spaced relation to electrode 24 and it is received within a rim-like structure 36 of insulative material, for example Teflon, for electrically insulating electrode 34 from the housing. An insulating epoxy 38 provided for positioning and holding electrode 34 in place. Electrode 34 also has a conical shaped outer surface 40 for a purpose to be described. A pin 41 fitted in the body of electrode 34 facilitates making electrical connection to a circuit in the apparatus.

The housing 20 has a main body portion provided with an interior chamber which contains a voltage source in the form of a battery designated 46 in broken lines. A sensing and firing circuit is provided on a board 50 shown in broken lines located in the main body portion near battery 46, and the circuit will be described in detail presently. The electrodes 24,34, battery 46, circuit and electro explosive device are connected electrically in a circuit in a manner which will be described.

Briefly summarizing the operation of the apparatus shown in FIGS. 1 and 2, when electrodes 24,34 are exposed to fluid such as water having predetermined conditions of electrical conductivity, the circuit functions to supply after a predetermined time a firing current to the electro explosive device to detonate the same. The resulting explosive force acting against the face of the piston shears the pin holding the same and drives the piston to the right as viewed in FIG. 1. This displaces the end of the piston from the aforementioned plug and the yoke arm to the point within the sleeve 14, thereby releasing the piston end, the left hand end as viewed in FIG. 1, of sleeve 14 from the buckle frame. After a short distance of axial travel within the sleeve 14, the opposite end of the piston strikes the end of the bushing shearing its pin and driving the bushing into the right as viewed in FIG. 1 out of the sleeve 14 thereby freeing the bushing end of sleeve 14 from the buckle frame. Sleeve 14 then drops free of of the buckle yoke releasing a load from the canopy. The piston and bushing are wedged and lodged in their respective release positions within the structure thereby precluding any possibility of rebound to interfere with release of the sleeve 14 from the buckle frame. For a more detailed description of the construction and operation of the canopy release mechanism shown in FIG. 1, reference may be made to U.S. Pat. No. 4,307,858 issued Dec. 29, 1981 entitled "Canopy Release Mechanism" and to pending U.S. patent application Ser. No. 207,340 filed Nov. 17, 1980 entitled "Fluid Conductivity Sensor" both assigned to the assignee of the present invention, the disclosures of both of which are hereby incorporated by reference.

Figure 4:
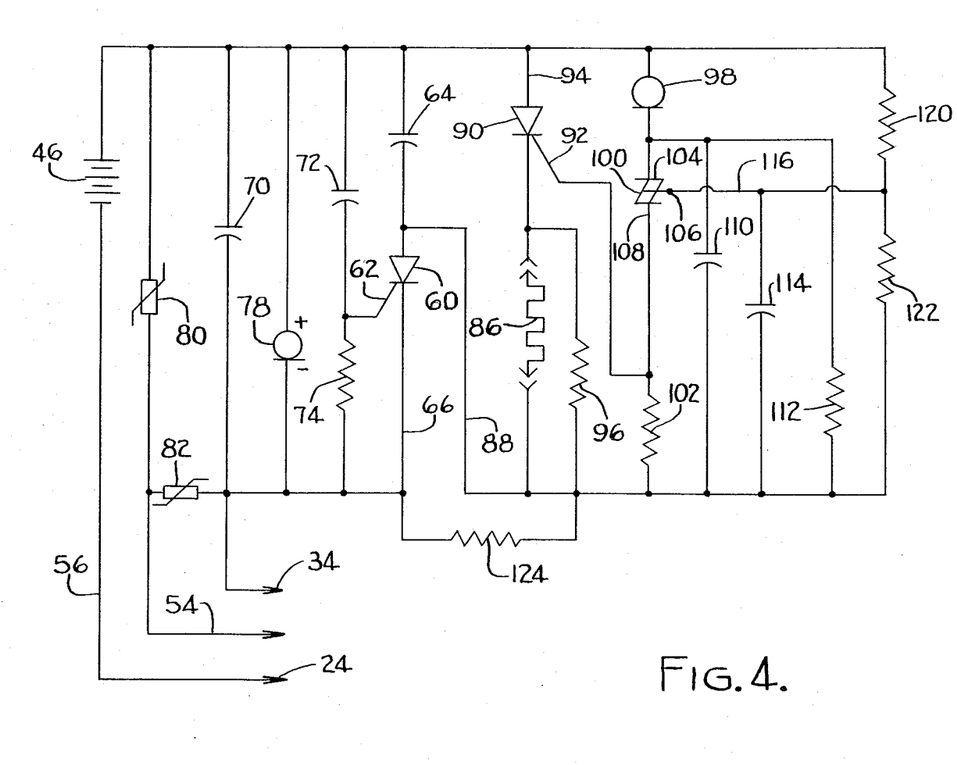
FIG. 4 is a schematic circuit diagram of apparatus for sensing electrical conductivity of fluid according to the present invention.

FIG. 4 illustrates in further detail the apparatus for sensing electrical conductivity of a fluid according to the present invention. The apparatus includes a pair of electrodes adapted to be exposed to the fluid. By way of example, when used in a canopy release mechanism as shown in FIG. 1, the electrodes are the sensing electrodes 24 and 34. In the circuit shown in FIG. 4, the housing 20 serves as a ground or reference, and line 54 connects a circuit reference point to housing 20. The apparatus further comprises a voltage source having a pair of terminals, one of which is connected to one of the afore-mentioned electrodes. In the circuit shown, the voltage source comprises a battery 46 and the negative terminal of battery 46 is connected by a conductor designated 56 to the electrode 24.

The apparatus further comprises a three terminal semiconductor device in the form of a silicon controlled rectifier generally designated 60. Controller rectifier 60 has an anode terminal, a cathode terminal and a control or gate terminal designated 62, and controlled rectifier 60 normally is in a non-conducting state and is adapted to be switched to a conducting state defining a current flow path between the anode and cathode terminals of the rectifier when a voltage of sufficient magnitude is applied to the gate terminal 62. The circuit further comprises a load connected electrically in series with the current flow path of the semiconductor device 60. In the circuit shown the load includes a capacitor 64 and portions of the circuit included to the right of device 60 as shown in FIG. 4 which will be described in detail presently. The combination of the load and the semiconductor device 60 is connected between the other terminal of the voltage source and the other one of the electrodes. In particular, one terminal of capacitor 64 is connected to the anode of controlled rectifier 60 and the other terminal of capacitor 64 is connected to the positive terminal of battery 46. The cathode of controlled rectifier 60 is connected by line 66 to sensing electrode 34.

The apparatus of FIG. 4 further comprises a conductivity sensing circuit connected to the other sensing electrode, i.e. electrode 34, to the other voltage source terminal, i.e. the positive terminal of battery 46, and to the gate terminal 62 of the semiconductor device 60. The circuit is responsive to the magnitude or degree of electrical conductivity of fluid to which the electrodes are exposed and to the time rate of change of conductivity in the medium to which the electrodes are exposed, and the circuit applies to the terminal 62 of semiconductor device 60 a voltage of sufficient magnitude to switch device 60 into the conducting state when the electrical conductivity of the fluid is of a predetermined minimum magnitude and when the rate of change in conductivity of the medium to which the electrodes are exposed is of a predetermined minimum magnitude. As a result of the device being switched to a conducting state, a flow of current is allowed through the load connected to device 60. The conductivity sensing circuit includes means having a time varying electrical characteristic wherein the rate of change of the characteristic is proportional to the magnitude or degree of electrical conductivity of the fluid to which the electrodes are exposed and to the rate of change in conductivity of the medium to which the electrodes are exposed. The voltage of sufficient magnitude for switching semiconductor device 60 is applied to terminal 62 of device 60 only when the rate of change of that electrical characteristic reaches a predetermined value.

In particular, the conductivity sensing circuit includes capacitive means having a charging rate responsive to the degree of magnitude of conductivity of the fluid to which the electrodes are exposed and to the time rate of change in conductivity of the medium to which the electrodes are exposed whereby when the degree or magnitude of conductivity is sufficiently large and the rate of change is sufficiently great, the rate of voltage rise on the capacitive means is sufficient to couple the gating or switching voltage to terminal 62 of device 60. In the circuit shown, the sensing circuit comprises a first capacitor 70 connected between electrode 34 and the positive terminal of battery 46. The sensing circuit further comprises the series combination of a second capacitor 72 and a resistor 74 connected between electrode 34 and the battery positive terminal. The gate terminal 62 of the device 60 is connected to the junction of capacitor 72 and resistor 74. The relative magnitudes of the first capacitor 70, second capacitor 72 and resistor 74 are selected such that the voltage on the second capacitor 72 cannot increase faster than the voltage on the first capacitor 70 and the charging rate of the second capacitor 72 is controlled by the first capacitor 70. A current regulating means in the form of current regulator diode 78 is between electrode 34 and the positive terminal of battery 46 and thus is in parallel with capacitor 70 and also in parallel with the series combination of capacitor 72 and resistor 74. The series combination of Varistors 80 and 82 is connected between the positive battery terminal and electrode 34 and serves to protect against static discharge. The junction of Varistors 80,82 is connected by line 54 to the housing 20.

In operation, when sensing electrodes 24 and 34 are exposed to fluid having at least some degree of electrical conductivity, there will be some flow of electrical current through the fluid between electrodes 24 and 34 and through the conductivity sensing portion of the circuit of FIG. 4. In particular, the electron flow is from the negative terminal of battery 46 through conductor 56 to electrode 24 and through the fluid to electrode 34 and then through the four parallel circuit paths to the positive terminal of battery 46. Those four paths include capacitor 70, current regulator diode 78, the combination of resistor 74 and capacitor 72, and the path defined by lead 66, the cathode-to-gate path of rectifier 60 and capacitor 72. However, under specified no-fire conditions as determined by the magnitudes of the circuit components, there will be insufficient energy coupled to the gate 62 of controlled rectifier 60 through capacitor 72 to turn the rectifier on and therefore no flow of current through the load, i.e. no charging or capacitor 64. By way of example, when the apparatus is used in a canopy release mechanism, the specified no-fire condition is water having a conductivity of 250 micro-mhos of less. After capacitors 70 and 72 are charged the current drain on battery 46 is limited by the resistance of the parallel combination of regulator 78 and Varistors 80,82. This quiesient condition will continue until the circuit is removed from the no-fire environment and the capacitors are allowed to reset.

In the illustrative use of the apparatus in a canopy release mechanism, the specified all fire condition is water having a conductivity of 10,000 micro-mhos or greater. When the electrodes are exposed to such water the rate of voltage rise on capcitor 70 becomes sufficient to couple the required energy through capacitor 72 to gate 62 of controlled rectifier 60 turning it on and thereby allowing the battery 46 to begin charging the capacitor 64. In addition, the exposure of the electrode to the electrically conductive fluid is under conditions where the rate of change of conductivity is at least a predetermined minimum value. For example, under conditions where the electrodes have been exposed to atmospheric air and suddenly are exposed to a static body of water having the aforementioned conductivity of 10,000 micro-mhos or greater, both the conductivity of the water and the time rate of change in the conductivity of air to the conductivity of the water are sufficiently great to couple the energy through capacitor 72 to gate rectifier 60 into conduction. In other words, as the parachute and person wearing same descend through air which is nonconductive and then suddenly enter a body of water such as the ocean, there is a very rapid rate of change in conductivity sensed by the electrodes and it is a sufficiently rapid rate of rise to cause gating of the rectifier 60 into conduction. However, when the electrodes are exposed first to air and then are exposed to rain, salt water spray or fog, the time rate of change in conductivity from air to the rain, salt water spray or fog is relatively slow and in any event not great enough to couple sufficient energy to gate rectifier 60 into conduction. Such conditions of rain, salt water spray and fog typically are encountered by stationary aircraft on a carrier vessel at sea.

In the operation of the sensing circuit to perform the foregoing conductivity and rate of change determinations, as previously mentioned the voltage or capacitor 72 cannot rise faster than the voltage on capacitor 70 and the charging rate of capacitor 72 is controlled by capacitor 70. The foregoing is believed to result from the selected magnitude of capacitor 70 and the conductivity of the fluid medium between the sensing electrodes relative to the selected magnitudes of capacitor 72 and resistor 74. In addition to the foregoing, Varistors 80,82, which preferably are of the metal oxide type, provide static supression, i.e. prevent inadvertent firing of rectifier 60 by the electrode being exposed to static electricity on people or other items which come into proximity to or in contact with the apparatus. The Varistors 80,82 protect against such discharge from electrode to electrode and from each electrode to the housing, and this protection is enhanced by the fact that the circuit of FIG. 4 is disengaged from the housing. In the general use of the circuit of the present invention, gating of rectifier 60 to allow current flow through a load, i.e. capacitor 64, is a signal that the fluid has the specified minimum conductivity and that the electrodes have been exposed to at least a certain time rate of change of fluid conductivity, and the signal can be utilized as such. In the illustrative use in a canopy release mechanism, charging of capacitor 64 initiates ignition of the electro explosive device in a manner which will be described.

The apparatus of FIG. 4 further comprises a two terminal electro explosive device 86, for example the electro explosive device mentioned in connection with the illustrative mechanism of FIG. 1. One terminal of device 86 is connected by means of conductor 88 to the terminal of capacitor 64 adjacent the anode of controlled rectifier 60. The circuit of FIG. 4 further comprises semiconductor switching means 90 connected to the other terminal of the electro explosive device 86 and to the other terminal of the ignition capacitor 64. The semiconductor switching means 90 normally is in a nonconducting state and is adapted to be switched to a conducting state when an electrical quantity of predetermined magnitude is applied to a control or gate terminal 92 thereof. In the circuit of FIG. 4, capacitor 64 functions as an ignition capacitor for the electro explosive device 86. In particular, capacitor 64 is charged at a rate proportional to the conductivity of the fluid and is charged to a predetermined value of charge while the semiconductor device 60 is in the conducting state. Capacitor 64 then is discharged through the electro explosive device 86 to detonate the same a predetermined thereafter. In particular, when the semiconductor switching means 90 is in the conducting state it defines a discharge path for the ignition capacitor 64 through the electro explosive device 86. The semiconductor switching means 90 comprises a controlled rectifier, and the anode terminal is connected by line 94 to ignition capacitor 64. The cathode terminal of controlled rectifier 90 is connected to a terminal of the electro explosive device. A safety or protective resistor 96 is connected across the electro explosive device 86 to prevent inadvertent firing. In particular, resistor 96 prevents a voltage build-up across the circuit connections to electro explosive device 86 when the device is removed during replacement or repair. Otherwise, if such build-up were allowed to occur, re-connection of device 86 could operate controlled rectifier 90 causing inadvertent firing of device 86.

The apparatus of FIG. 4 further comprises an operating network connected to the ignition capacitor 64 and to the conductivity sensing circuit and connected in controlling relation to the semiconductor switching means 90 for causing the semiconductor switching means to switch to the conducting state to define the discharge path to activate the electro explosive device 86 in a controlled manner. The operating network has a voltage independent portion including timing means which functions to activate the electro explosive device 86 a predetermined time after initiation of charging of the ignition capacitor 64 independent of the rate of charging of the ignition capacitor 64. The operating network also has a voltage dependent portion which by-passes the silicon-controlled rectifier 60, and when a voltage of predetermined magnitude is developed on the conductivity sensing circuit when electrodes 24,34 are exposed to fluid having conductivity below a predetermined level, the voltage dependent portion operates semiconductor switching means to cause current flow through electro-explosive device 86 but at level of energy below that required for activation of device 86.

As shown in FIG. 4, the operating network includes a branch comprising the series combination of a current regulating device 98, a three terminal semiconductor switch 100 and a resistor 102, and the branch or combination is connected across or in parallel with the series combination of controlled rectifier 90 and electro explosive device 86. Semiconductor switch 100 has anode, gate and cathode terminals 104,106 and 108, respectively. The anode terminal 104 is connected to one terminal of current regulating device 98, and the other terminal of device 98 is connected to the anode of controlled rectifier 90. The cathode terminal 108 of semiconductor switch 100 is connected to one terminal of resistor 102, and the other terminal of resistor 102 is connected to the junction of line 88 and the terminals of electro explosive divice 86 and protective resistor 96.

The operating network also includes the parallel combination of a capacitor 110 and a resistor 112 connected across the combination of semiconductor switch 100 and resistor 102. One terminal of capacitor 110 is connected to the anode 104 of semiconductor switch 100, and the other terminal of capacitor 110 is connected to the other terminal of resistor 102. Resistor 112 is connected across capacitor 110. The operating network also includes a capacitor 114, one terminal of which is connected by line 116 to the gate terminal 106 of semiconductor switch 100, and the other terminal of which is connected to the other terminal of resistor 102. The operating network is completed by a voltage divider operatively connected to the conductivity sensing circuit and connected in controlling relation to the gate terminal 106 of semiconductor switch 100. The voltage divider comprises the series combination of resistors 120,122 and 124. One end of the voltage divider, in particular one terminal of resistor 120, is connected to the junction of current regulating device 98 and the anode of semiconductor switch 90. The other end of the voltage divider, in particular one terminal of resistor 124, is connected to the cathode of controlled rectifier 60. The junction of resistors 120 and 122 of the voltage divider is connected to gate terminal 106 of semiconductor switch 100 through lines 126 and 116.

The operating network has various modes of operation for assuring that the electro explosive device 86 is activated, i.e. detonated, only in response to the predetermined conditions of fluid conductivity senses by electrodes 24,34 and the sensing circuit and that the device 86 is not detonated prematurely or inadvertently. During an all-fire mode of operation, the function of the circuit of FIG. 4 is to provide ignition energy to electro explosive device 86 when the apparatus is subjected to rapidly changing conductive environment. In particular, when electrodes 24,34 are subjected to fluid of rapidly increasing electrical conductivity, capacitor 70 charges quickly and the charging time is limited essentially by the conductivity between electrodes 24,34. If the conductivity is high enough, for example greater than 10,000 micro mhos, a portion of the signal charging capacitor 70 is coupled through capacitor 72 across resistor 74 and the gate/cathode connections of controlled rectifier 60 turning the rectifier on. Operation of controlled rectifier 60, in turn, allows the ignition capacitor 64 to charge up and it also supplies power to a time delay portion of the operating network in the circuit of FIG. 4. In particular, the time delay portion includes current regulating device 98 and semiconductor switch 100, capacitor 110, resistor 112, capacitor 114 and the resistors 120 and 122 of the voltage divider. After a predetermined time delay, preferably about 1.2 seconds, semiconductor switch 100 is closed with the result that the time delay portion provides controlled rectifier 90 with a turn-on pulse at resistor 102. Operation of controlled rectifier 90 completes a discharge path for stored energy from capacitor 64 through electro explosive device 86 causing explosive ignition thereof and functioning of the parachute canopy release mechanism previously described.

During the foregoing operation, as the charge on the ignition capacitor 64 increases over time, the increasing voltage across capacitor 64 is reflected across the timing network described above. Although the rate of voltage rise on the ignition capacitor 64 is exponential and a function of the conductivity of the fluid to which the electrodes 24,34 are exposed, the current regulating device 98 causes the rate of voltage rise on capacitor 110 to be essentially constant over a widely changing range of applied voltage. The rate of voltage rise on capacitor 114 also is constant until it reaches the level determined by the relative magnitudes of resistors 120 and 122 whereupon the capacitor voltage is limited to that level or plateau. When the increasing voltage on capacitor 110 reaches a value exceeding the voltage level on capacitor 114 by an amount equal to the anode-gate switching voltage of semiconductor device 100, the device will turn on discharging capacitor 110 through resistor 102 causing a voltage/current pulse on the control terminal 92 of controlled rectifier 90 causing it to turn on. When controlled rectifier 90 is turned on, the capacitor 64 discharges through the controlled rectifier 90 and the electro explosive device 86 thereby causing explosive ignition of the device 86. By way of example, in an illustrative circuit, semiconductor switch 100 is turned on when the gate voltage is 0.6 volts negative with respect to the anode voltage.

Figure 5:
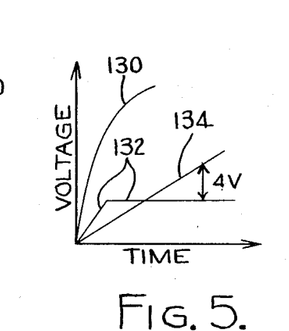
FIG. 5 is a graph including waveforms illustrating operation of the circuit of FIG. 4 during one mode.

The foregoing is illustrated further in FIG. 5 which includes waveforms of the build-up of voltage over time on the capacitors 64, 110 and 114 during the all-fire mode. Waveform 130 illustrates the relatively fast, exponential build-up of voltage on ignition capacitor 64 as previously described. Waveform 132 shows the relatively linear build-up of voltage on capacitor 114, which is connected to the gate terminal of semiconductor switch 100, until that voltage reaches the level or plateau determined by the voltage divider network. Waveform 134 illustrates the relatively linear build-up of voltage on capacitor 110, which is connected to the anode terminal of semiconductor switch 100. The build-up of the voltage on capacitor 110 is slower than the build-up on capacitor 114, and since capacitor 110 is not connected to the voltage divider it continues to build-up linearly. By way of example, in an illustrative circuit, the anode time constant for semiconductor switch 100 is 1.2 seconds and the gate time constant is 0.59 seconds. When the voltage on the gate of switch 100 becomes negative with respect to the voltage on the anode of switch 100 by a predetermined amount $\Delta V$, semiconductor switch 100 closes to cause the operation of the other components of the network as previously described. By way of example, in an illustrative circuit $\Delta V$ is 0.6 volts.

The timing means thus provides a time delay which gives ignition capacitor 64 sufficient time to charge up to a level sufficient to provide the desired energy for firing the electro explosive device, that level preferably being at or near the voltage of battery 46. By way of example, in an illustrative circuit, the time delay from the beginning of charging of ignition capacitor 64 to the detonation of device 86 is 1.2 seconds in the all-fire mode described above. The timing means thus insures that electro explosive device 86 is effectively detonated with the proper desired level of energy or voltage and is not detonated until that specified level is reached. The timing means also serves to prevent accidental detonation of device 86 in response to a component failure or other circuit malfunction which improperly places a voltage across ignition capacitor 64 which voltage over a period of time could build up to a level sufficient to cause unwanted and accidental detonation of device 86. In particular, under such conditions where the circuit would attempt to fire the electro explosive device when such firing is not wanted, the time delay period built into the timing network, i.e. the 1.2 seconds period previously mentioned, will cause controlled rectifier 90 to fire at a time when the voltage on the ignition capacitor 64 is well below the voltage required for firing the electro explosive device so that the device is not fired. For example, assume that the electrodes 24,34 are exposed to water having an electrical conductivity below that at which it is desired to fire the electro explosive device. There will be a voltage drop between the electrodes and there also will be a voltage drop across ignition capacitor 64 due to the component failure. This voltage drop across capacitor 64, however, will be less, for example eight volts, than the voltage across capacitor 64 under all fire conditions with no component failure. But with the component failure and the passage of time the voltage on capacitor 64 could rise to a level sufficient to detonate the electro explosive device. The provision of the timing means prevents this because it causes controlled rectifier 90 to switch on after a preset time, for example 1.2 seconds, which time is well before the time when the voltage on capacitor 64 would reach a firing level.

During the no-fire mode of operation, the function of the circuit of FIG. 4 is to prevent explosive ignition of electro explosive device 86. This would of course occur during normal dry atmospheric conditions where the circuit is completely dormant due to the fact that sensing electrodes 24,34 being exposed to dry atmosphere are insulated from each other with the result that the negative terminal of battery 46 is separated from the circuit of FIG. 4 by the insulated sensing probes 24,34. This also occurs when the environment becomes slightly conductive, such as when electrodes 24,34 are exposed to rain, salt water spray and fog. The circuit also serves to prevent accidental detonation of electro explosive device 86 in response to a component failure or other circuit malfunction. For example, such situations can involve a slow build-up of charge on capacitor 70 during slightly conductive conditions such as rain, salt water spray and fog followed by a component failure placing the voltage built-up on capacitor 70, which could be nearly the battery voltage after a significant build-up time, across the operating portion of the circuit. In particular, during exposure of electrodes 24,34 to salt fog, for example, the rate of charge in electrical conductivity of the fluid to which the electrodes 24,34 are exposed is too slow to place the circuit in the all-fire mode. However, after such exposure, for a prolonged period of time, capacitor 70 can become highly charged and there is practically zero resistance between electrodes 24,34 with the result that practically the entire voltage of battery 46 is placed across the branch of the circuit including silicon controlled rectifier 60 and ignition capacitor 64. Controlled rectifier 60 has not been turned on, however, because the rate of change in conductivity of the fluid on electrodes 24,34 has been too slow. However, in the event of a component failure, such as break down or shorting of controlled rectifier 60 or shorting of capacitor 62, the entire battery voltage could be applied across the operating portion of the circuit thereby causing unwanted detonation of electro explosive device 86.

Accordingly, in the no-fire mode of operation, when the environment becomes slightly conductive so that one or two volts are present across capacitor 70, current will flow through resistors 124 and resistors 112, through the current regulating device 98, and through resistors 122 and 120. If the conductivity of fluid contacting electrodes 24,34 increases to a point where the relative voltages developed across capacitors 110 and 114 provide the required anode-gate voltage difference on semiconductor switch 100, the switch 100 is turned on and provides a discharge path for capacitors 110 and 114 through resistor 102. This, in turn, fires controlled rectifier 90 completing a discharge path for ignition capacitor 64 through electro explosive device 86 causing a nominal no-fire energy pulse through device 86. Thus, rectifier 90 is turned on to cause current flow through device 86 early, i.e. before the voltage on capacitors 70 builds up to a dangerously high level. By way of example, the nominal no-fire energy during the illustrative operation described above is approximately 0.0053 joules and the maximum no-fire energy specified for device 86 typically is 0.050 joules.

Figure 6:
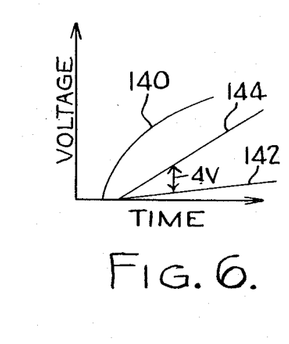
FIG. 6 is a graph including waveform illustrating operation of the circuit of FIG. 4 during a different mode.

The foregoing is illustrated further in FIG. 6 which includes waveforms of the build-up of voltage over time on the capacitors 64, 110 and 114 during the no-fire situation described above. Waveform 140 illustrates the relatively slow build-up voltage on capacitor 64 as previously described. When electrodes 24,34 are exposed to relatively lower conductivity fluid during these conditions, this is seen by the circuit as a relatively high resistance between the electrodes and hence an increase in the resistance in series with capacitor 114. This, in turn, increases the time constant of the gate circuit of semiconductor switch 100 resulting in a relatively slower linear build-up of voltage on capacitor 114 illustrated by waveform 142 in FIG. 6. With respect to capacitor 110 in the anode circuit of switch 100, however, although this portion of the network also sees a higher series resistance due to electrodes 24,34 being exposed to lower conductivity fluid, current source 98 compensates for this by tending to maintain the current constant and thereby keeping the anode time constant at about the same magnitudes as for all fire conditions. This is illustrated by the waveform 144 in FIG. 6. As a result, the voltage on gate termninal 106 of switch 100 is negative with respect to the anode voltage by the amount ΔV at a much earlier time as illustrated in FIG. 6.

During the foregoing operation in response to salt fog or other no fire conditions, the portion of the network including resistor 124 may be viewed as a means for bypassing controlled rectifier 60 with a relatively high resistance. During such conditions, the flow of current through resistor 124, resistor 102, and current source 98 causes semiconductor switch 100 to operate with a low voltage. The resistors 120 and 122 of the voltage divider network lower the voltage of which semiconductor device 100 will switch. Thus, the slowly rising voltages on capacitors 114 and 110 applied to the gate and anode, respectively, of semiconductor switch 100 coact with the voltage dividing action of resistors 120 and 122 to switch device 100 at a relatively low voltage applied across the network. During such slow voltage rise, semiconductor switch 100 is normally open, and the network includes one branch for current flow through resistors 120,122 and 124. Current source 98 initially is a short circuit and therefore another branch for current flow includes resistors 112 in parallel with resistors 120 and 122. The voltage on the gate terminal of semiconductr switch 100 is a portion of the voltage on the input or sensing capacitor 70 which portion is determined by the voltage divider network. The time relationship between resistor 124, the low resistance of controlled rectifer 60 when firing, and the capacitor 64 prevents resistor 124 and components associated therewith from having any effect on normal operation of the circuit during the all-fire mode. In particular, during normal operation of controlled rectifier 60 it goes from a resistance of greater than 10 megohms to about 3.5 ohms when fired. The time constant provided by the resistance of controlled rectifier 60 and capacitor 64 during normal is 2.3 miliseconds i.e. the time of firing. On the other hand, the time constant during the no-fire mode of operation when resistor 124 plays a role in the operation is about 31 milliseconds.

The foregoing mode of operation may be viewed as voltage dependent for the reason that operation of the semiconductor switch 100 to cause a nominal no-free energy pulse to flow through device 86 is in response to the voltage at the input portion of the circuit of FIG. 4 reaching a pre-determined magnitude. When the foregoing mode of operation occurs, the circuit has a latching or holding function which serves to keep switch 100 open with the result that no additional gating or turn on pulses are applied to gate 92 of controlled rectifier. This function is provided by the voltage divider whereby the magnitude of resistors 120,122 are selected to maintain the required anode-gate voltage differential on switch 100 to keep it closed once the foregoing operation has concluded. From another point of view, the switch 100 has a certain minimum holding current and the magnitudes of resistors 120,122 are selected to maintain that current even if the voltage on the anode of switch 100 falls below the switching level. The regulated current source 98 also plays a role in providing a minimum holding current to semiconductor switch 100. Thus, the network includes latching a holding circuit means in the form of resistors 120,122 and regulated current source 98 which, alone or in combination, function to keep semiconductor switch 100 closed, after the voltage dependent mode of operation has occurred, either by maintaining a predetermined holding current through switch 100 or by maintaining the required anode-gate voltage differential on switch 100.

Thus, under specified all-fire condition, the circuit of FIG. 4 operates in a voltage independent mode to cause explosive ignition of device 86, such all-fire conditions typically being fluid having a conductivity of greater than 10,000 micro mhos under conditions of rapidly changing conductivity. Under specified no-fire conditions the circuit of FIG. 4 operates in a voltage dependent mode to cause a nominal no-fire energy pulse to flow through device 86 with no ignition thereof, and this is followed by the latching or holding mode whereby the circuit will not provide any further turn on pulses to controlled rectifier 90 until the circuit is reset. Such no-fire conditions typically are the salt fog environmental conditions previously described and fluid having a conductivity of 1000 micro-mhos or less.

There is a range within the specified no-fire conditions where it is desired to prevent the circuit from being placed in the latching or lockout state. Physically, this would be a situation where a person is parachuting from an aircraft through rain toward a body of water. Obviously, it is important to prevent the circuit from entering the lockout state during the brief exposure to rain during descent. Thus a conductivity range is determined in which it is desired to prevent the latching or lockout operation, and in the illustrative use with a canopy release mechanism this is fluid having a conductivity of 250 micro mhos or less which is believed sufficiently adequate to include all situations and conditions involving descent through rain.

The foregoing is accomplished by having the entire voltage maintained between electrodes 24,34 when the electrodes are exposed to fluid having conductivity in the predetermined low range, i.e. the 0–250 micro mhos exemplary range mentioned above, and then having the entire voltage placed across the circuit for normal operation of the circuit when the fluid conductivity is above that range, i.e. greater than 250 micro mhos. Accordingly, there is provided current regulating means in the form of current regulating diode 78 connected across the conductivity sensing circuit for placing the circuit voltage across electrodes 24,34, when the conductivity of the fluid is below a predetermined magnitude and for placing all or substantially all of the voltage across the sensing circuit when the conductivity of the fluid is greater than a predetermined magnitude. The current regulating diode 78 acts as a short circuit when the voltage across the circuit is zero in response to electrodes 24,34 being exposed to fluid having zero conductivity. As the fluid conductivity increases the diode 78 continues to act as a short circuit until the predetermined conductivity level is reached whereupon diode 78 thereafter acts as a variable resistance of rapidly increasing magnitude to maintain a level of current corresponding to that level of fluid conductivity. Since the diode 78 acts as a short circuit until the predetermined level of conductivity is reached, during that time all of the voltage appears between electrodes 24,34 because there are zero volts across diode 78. When the predetermined level of conductivity is reached, thereafter the resistance of diode 78 increases and the proportion of the voltage across diode 78 and hence across the circuit of FIG. 4 increases thereby providing regular operation thereafter.

The foregoing is illustrated by the following example. Assume a voltage of 25 volts provided by battery 46 and that until the fluid conductivity reaches 250 micro mhos the entire or substantially the entire voltage is to be maintained between electrodes 24,34 with little or no voltage appearing across the remainder of the circuit. Having a conductivity of 250 micro mhos between electrodes is the equivalent of 4000 ohms. Since no voltage is to appear across the circuit of a voltage of zero volts must be across regulator diode 78 with the result that a current of 6.2 milliamperes must flow through the circuit including battery 46 which has a voltage of 25 volts, diode 78 and the resistance of 4000 ohms provided by the fluid between electrodes 24,34. At levels of fluid conductivity below 250 micro mhos, the resistance between electrodes 24,34 will be greater thereby resulting in a smaller current flowing through the above-defined circuit. Thus, current regulator diode 78 must act like a short circuit in the range of fluid conductivity from 0–250 micro mhos corresponding to a circuit flow in the range from 0–6.2 milliamperes. Once the fluid conductivity exceeds 250 micro mhos, corresponding to a current flow greater than 6.2 milliamperes, current regulator diode 78 changes from a short circuit or zero resistance condition rapidly to a resistance magnitude of about 4000 ohms. This maintains a current of 6.2 milliampere regardless of the amount by which the conductivity of fluid between electrodes 24,34 increases thereby placing all or substantially all of the voltage across the circuit in parallel with diode 78.

Thus, the provision of current regulator diode 78 keeps the input voltage across the sensing electrodes 24,34 during a predetermined range of conductivity of fluid to which electrodes 24,34 are exposed. This, in turn, prevents operation of the voltage dependent portion and lock-out functions of the circuit of FIG. 4 until electrodes 24,34 are exposed to fluid having a conductivity exceeding the predetermined range. As a result, the voltage dependent portion of the circuit of FIG. 4 and the lockout function provided thereby do not interfere with normal operation of the apparatus. In particular, as illustrated in the foregoing example, normal operation of the apparatus is ensured in a situation where a person parachutes through a rainstorm into a body of water.

In the conductivity sensing portion of the circuit of FIG. 4, resistor 74 is of a relatively large magnitude selected to provide increased gate sensitivity for controlled rectifier 60. This, in turn, avoids problems in circuit operation in response to direction change of electrodes 24,34 once they enter a body of water. In particular, when a person parachuting first lands in a body of water his initial direction is downward, then there is a reversal to upward movement caused by buoyancy and possibly by the action of the parachute, and then further alternating downward and upward movements of decreasing magnitude until equilibrium is reached. With the apparatus being carried by the person, the electrodes 24,34 experience these same movements relative to the fluid, and these movements even can include brief excursions above the water level such that for brief intervals the electrodes 24,34 are not exposed to the water. The gate sensitivity of controlled rectifier 60 is increased to avoid any adverse effects on sensing circuit operation due to the foregoing alternating movements. In particular, once the person lands in the water it is desired to have the parachute release mechanism operated as soon as required according to specifications, without any delay caused by the foregoing alternating movements. In the sensing circuit, capacitor 70 serves as a source for charging capacitor 72.

When the conductivity sensing apparatus of the present invention is used for detonating an electro explosive device in a canopy release mechanism as previously described, the voltage source is in the form of a battery. It would be highly desirable to maximize use of the available battery voltage, i.e. have ignition capacitor 64 charge to a value as close as possible to the full voltage of battery 42 during the all-fire mode of operation. Maximizing the voltage on capacitor 64 of course maximizes the energy for detonating electro explosive device 86. In accordance with the present invention, it has been found that having electrodes 24,34 of dissimilar metals enables ignition capacitor 64 to change to a voltage closer to the full value of battery 46, as compared to the situation where electrodes 24,34 are of the same metal. Furthermore, it is believed that this battery voltage utilization is further enhanced by having the electrode of metal which is lower in the electromotive series connected to the negative battery terminal and by having the electrode of metal relatively higher in the electromotive series coupled through the circuit to the positive battery terminal. In the apparatus shown, electrode 24 is of a stainless steel and is connected directly to the negative terminal of battery 46. Electrode 34 is of aluminum and is coupled through the sensing circuit to the positive terminal of battery 46. With these metals selected for electrodes 24,34 and with the electrical connections as specified, it has been found that ignition capacitor 64 can be charged to a voltage within a few tenths of the 25 volts provided by battery 46 in the foregoing example. This is in contrast to prior apparatus wherein with sensing electrodes of the same metal the ignition capacitor would change to a voltage 1½ to 2 volts less than the battery voltage. Also, it has been determined that reversing the connections of the aluminum and stainless steel electrodes, i.e. aluminum electrode to negative battery terminal and stainless steel electrode through current to positive battery terminal, would result in ignition capacitor 64 reaching a voltage of only 21–22 volts during all fire condition with a battery of 25 volts. The convex and conical surfaces 30 and 40 of electrodes 24,34 respectively, provide increased electrode operative surface for increased fluid sensing efficiency and in a manner which prevents any accumulation of debris or similar contamination on the electrode surfaces.

By way of example, in an illustrative circuit for use in a canopy release mechanism, electrode 24 is of stainless steel, electrode 34 is of aluminum, battery 46 has a magnitude of 25 volts, capacitor 70 has a magnitude of 78 microfarads at 50 volts d.c., capacitor 72 has a magnitude of 1.0 microfarad at 50 volts d.c. and resistor 74 has a magnitude of 22 kilohms. Varistors 80,82 are of metal oxide type commercially available from the General Electric Co. under the designation V68MA3A and current regulator diode 78 is commercially available from Crystalonics under the designation C1L-252 and rated at 6.2 milliamperes. Capacitor 64 has a magnitude of 660 microfarads at 15 volts d.c. and silicon controlled rectifier 60 is of the type General Electric 2N880. Silicon controlled rectifier 90 is of the type RCA 52600D, electro explosive device 86 is Conax CC131, current regulator 98 is a current regulator diode commercially available from Motorola under the designation 1N5289 and rated at 0.43 milliamperes and semiconductor switch 100 is a silicon unilateral switch commercially available from General Electric under the identification 2N4985. Capacitors 110 and 114 have magnitudes of 66 microfarads and 33 microfarads, respectively, at 10 volts, resistors 96,102 and 112 have magnitudes of 1.0 kilohms, 10 ohms and 100 kilohms, respectively, and resistors 120,122 and 124 have magnitudes of 18 kilohms, 68 kilohms and 47 kilohms, respectively.

It is therefore apparent that the present invention accomplishes its intended objects. While an embodiment of the present invention has been described in detail, this is for the purpose of illustration, not limitation.

I claim:

1. A circuit for activating a device in response to a predetermined condition in the electrical conductivity of a fluid comprising:
   (a) electrode means adapted to be exposed to said fluid;
   (b) a conductivity sensing circuit having an input operatively connected to said electrode means and being responsive to a predetermined condition of the conductivity of said fluid, said circuit including energy storage means for storing electrical energy building up when said electrode means is exposed to an electrically conductive fluid;
   (c) a current conducting device activated in response to electrical energy of a predetermined minimum magnitude being applied thereto; and
   (d) circuit means connected to said conductivity sensing circuit and to said current conducting device;
   (e) said circuit means having a first portion operative in response to said predetermined condition of the conductivity of said fluid as sensed by said conductivity sensing circuit for applying to said device electrical energy of sufficient magnitude to activate said device;
   (f) said circuit means having a second portion responsive to a predetermined level of energy in said energy storage means when the conductivity of said fluid is less than said predetermined condition for causing flow of current through said device in a manner applying to said device electrical energy having less than said predetermined minimum magnitude required to activate said device;
   (g) whereby a build-up of energy on said energy storage means in response to fluid having a conductivity less than said predetermined condition is removed from said energy storage means and conducted through said device without activating said device so as to prevent premature activation of said device.

2. Apparatus according to claim 1, wherein said circuit means includes ignition energy storage means and controlled semiconductor switching means for providing a discharge path from said ignition energy storage means to said device and wherein said first portion of said circuit means includes timing means connected in controlling relation to said switching means for causing operation of said switching means to complete said discharge path a predetermined time after initiation of charging of said ignition energy storage means independent of the rate of charging of said ignition energy storage means.

3. Apparatus according to claim 2, wherein said timing means comprises:
(a) a semiconductor switch having anode, gate and cathode terminals;
(b) current regulating means connected between said conductivity sensing circuit and the anode of said semiconductor switch;
(c) an RC circuit connected to the anode of said semiconductor switch;
(d) a capacitive circuit connected to the gate of said semiconductor switch;
(e) means for connecting the cathode of said semiconductor switch in controlling relation to said controlled semiconductor switching means; and
(f) a resistive circuit connected across the combination of said semiconductor switch and said current regulating means.

4. Apparatus according to claim 1, wherein said circuit means includes ignition energy storage means and controlled semiconductor switching means for providing a discharge path from said ignition energy storage means to said device and wherein said second portion of said circuit means includes voltage responsive circuit means connected to said sensing circuit and connected in controlling relation to said switching means for causing operation of said switching means to conduct current through said device at a time when the energy level is insufficient to activate said device.

5. Apparatus according to claim 4, wherein said voltage responsive circuit means comprises:
(a) a first branch including a semiconductor switch having anode, gate and cathode terminals;
(b) a relatively high resistance branch connected to said conductivity sensing circuit and having a portion connected across said first branch;
(c) an RC circuit connected to the anode of said semiconductor switch and to said high resistance branch;
(d) a capacitive circuit connected to the gate of said semiconductor switch;
(e) means for connecting the cathode of said semiconductor switch in controlling relation to said controlled semiconductor switching means; and
(f) means for connecting the gate of said semiconductor switch to a point within said portion of said high resistance branch;
(g) whereby the rising voltages on said circuits connected to said anode and gate of said semiconductor switch coact with the voltage dividing action of the connection of said portion of said high resistance branch to said gate of said semiconductor switch to operate said semiconductor switch at a relatively low voltage applied across voltage responsive circuit means.

6. Apparatus according to claim 1, wherein said second portion of said circuit means includes latching circuit means for preventing further flow of energy to said device after operation of said second portion of said circuit means.

7. Apparatus according to claim 6, further including current regulating means connected across said conductivity sensing circuit and to said electrode means, said current regulating means placing the entire circuit voltage on said electrode means when the conductivity of the fluid is below a selected level of magnitude which is below the magnitude corresponding to said predetermined condition of conductivity, said current regulating means placing substantially the entire circuit voltage across said sensing circuit when the conductivity of the fluid is above said selected level of magnitude, whereby said conductivity sensing circuit does not respond to fluid conductivity below said selected level of magnitude.

8. Apparatus according to claim 7, wherein said current regulating means comprises a current regulator diode, said diode acting as a short circuit when the fluid conductivity is below said selected level of magnitude and said diode acting as a rapidly increasing resistance when the fluid conductivity is above said selected level of magnitude.

9. Apparatus according to claim 1, wherein said circuit means comprises:
(a) ignition energy storage means and controlled semiconductor switching means connected to said ignition energy storage means and to said device for providing a discharge path from said ignition energy storage means to said device;
(b) a semiconductor switch having anode, gate and cathode terminals, said switch being normally open and operative to close in response to a predetermined voltage difference applied between said anode and gate terminals;
(c) current regulating means connected to said ignition energy storage means and said anode terminal of said semiconductor switch;
(d) means for connecting the cathode terminal of said semiconductor switch in controlling relation to said controlled semiconductor switching means;
(e) a relatively high resistance circuit branch connected at one end to said ignition energy storage means and at the other end to said conductivity sensing circuit;
(f) a parallel RC circuit connected to the anode terminal of said semiconductor switch and to said resistance circuit branch;
(g) a capacitive circuit connected to the gate terminal of said semiconductor switch and to said resistance circuit branch; and
(h) means for connecting the gate terminal of said semiconductor switch to a point in said resistance branch circuit.

10. Apparatus according to claim 1, wherein said current conducting device is an electro explosive device which is detonated when said electrical energy of said predetermined minimum magnitude is applied thereto.

11. Apparatus according to claim 10, wherein said electro explosive device is included in a release mechanism for uncoupling a parachute canopy from its load upon landing in water, said canopy being uncoupled when said electro explosive device is detonated, and said electro explosive device being detonated when said electrode means is exposed to water having said predetermined condition of conductivity.

12. Apparatus for sensing the electrical conductivity of fluid comprising:
(a) a pair of electrodes adapted to be exposed to said fluid;
(b) a voltage source having a pair of terminals, one of said terminals being connected to one of said electrodes;

(c) a conductivity sensing circuit connected to the other electrode and to the other terminal of said voltage source, said circuit being responsive to the electrical conductivity of fluid to which said electrodes are exposed, said circuit providing an electrical signal when the electrical conductivity of the fluid is at or above a first level of magnitude; and (d) current regulating means connected across said conductivity sensing circuit, said current regulating means placing the entire circuit voltage across said electrodes when the conductivity of the fluid is below a second level of magnitude and placing substantially the entire circuit voltage across said sensing circuit when the conductivity of the fluid is above said second level of magnitude, said second level of magnitude being lower than said first level of magnitude;

(e) whereby said conductivity sensing circuit does not respond to fluid conductivity below said second level of magnitude.

13. Apparatus according to claim 12, wherein said current regulating means comprises a current regulator diode, said diode acting as a short circuit when the fluid conductivity is below said second level of magnitude and said diode acting as a rapidly increasing resistance when the fluid conductivity is above said second level of magnitude.

14. Apparatus according to claim 12, further comprising:

(a) semiconductor switching means normally in a nonconducting state and adapted to be switched to a conducting state defining a current flow path there through when a switching voltage of sufficient magnitude is applied thereto;

(b) a load connected electrically in series with the current flow path of said semiconductor switching means;

(c) said load and said semiconductor switching means being connected between said other terminal of said voltage source and said other one of said electrodes; and (d) said conductivity sensing circuit being connected in controlling relation to said semiconductor switching means for applying to said switching means said switching voltage of sufficient magnitude to place said switching means in said conducting state when the electrical conductivity of said fluid is of a predetermined minimum magnitude.

15. Apparatus according to claim 14, further including an electro explosive device, said load comprising circuit means connected to said electro explosive device for supplying current to said electro explosive device to detonate said explosive device after said semiconductor switching means is switched to the conducting state.

16. Apparatus according to claim 15, wherein said electro explosive device is included in a release mechanism for uncoupling a parachute canopy from its load upon landing in water, said canopy being uncoupled when said electro explosive device is detonated, and said electro explosive device being detonated when said electrodes are exposed to water having a conductivity at or above said first level of magnitude.

17. Apparatus for sensing the electrical conductivity of fluid comprising:

(a) a pair of electrodes adapted to be exposed to said fluid;

(b) a voltage source having a pair of terminals, one of said terminals being connected to one of said electrodes;

(c) a three terminal semiconductor device normally in a nonconducting state and adapted to be switched to a conducting state defining a current flow path between two terminals of said device when a voltage of sufficient magnitude is applied to a gate terminal of said device;

(d) a load connected electrically in series with the current flow path of said device;

(e) said load and said semiconductor device being connected between the other terminal of said voltage source and the other one of said electrodes; and (f) a conductivity sensing circuit connected to said other electrode, to said other voltage source terminal and to said gate terminal of said semiconductor device, said circuit being responsive to the electrical conductivity of fluid to which said electrodes are exposed and to the rate of change in electrical conductivity to which said electrodes are exposed for applying to said gate terminal of said semiconductor device a voltage of sufficient magnitude to switch said device to said conducting state when the electrical conductivity of said fluid and the rate of change in electrical conductivity each is of a predetermined minimum magnitude thereby allowing a flow of current through said load;

(g) said sensing circuit comprising a series combination of a capacitor and a resistor connected between said other electrode and said other terminal of said voltage source, said gate terminal of said semiconductor device being connected to the junction of said coupling capacitor and said resistor;

(h) said resistor being of a relatively large magnitude selected to provide enhanced gate sensitivity for said semiconductor device whereby said apparatus is not adversely influenced by changes in direction of movement of said electrodes in a body of said fluid or alternate rapid movements of said electrodes into and out of a body of said fluid.

18. Apparatus according to claim 17, further including another capacitor connected between said other electrode and said other terminal of said voltage source, said other capacitor serving as a source for charging said first-named capacitor.

19. Apparatus according to claim 17, further including an electro explosive device, said load comprising circuit means connected to said electro explosive device for supplying current to said electro explosive device to detonate said explosive device after said semiconductor device is switched to the conducting state.

20. Apparatus according to claim 19, wherein said electro explosive device is included in a release mechanism for uncoupling a parachute canopy from its load upon landing in water, said canopy being uncoupled when said electro explosive device is detonated, and said electro explosive device being detonated when said electrodes are exposed to water having a predetermined conductivity under exposure conditions involving a predetermined rate of change in conductivity.

21. In apparatus including a circuit for sensing electrical conductivity of fluid wherein when a pair of electrodes is exposed to a conductive fluid a semiconductor device is switched into conduction to define a current path from a battery through a load including an ignition capacitor for detonating an electro explosive device for operating a mechanism associated with life support apparatus upon landing in water, the improvement that said electrodes are of dissimilar metals so selected and so connected to said battery and to said circuit to maximize the amount of voltage from said battery used in charging said ignition capacitor.

22. Apparatus according to claim 21, wherein one of said electrodes is connected to the negative terminal of said battery and the other of said electrodes is coupled through said circuit to the positive terminal of said battery, the metal of said one electrode being lower in the electromotive series than the metal of said other electrode.

23. Apparatus according to claim 22, wherein said one electrode is of stainless steel and said other electrode is of aluminum.

24. Apparatus according to claim 21, wherein the surfaces of said electrodes exposed to fluid are convex conical.

* * * * *